(12) United States Patent
Zhao et al.

(10) Patent No.: US 6,412,131 B1
(45) Date of Patent: Jul. 2, 2002

(54) MICROELECTROMECHANICAL MECHANISMS FOR REAL-TIME MECHANICAL VIBRATION SIGNATURE MONITORING AND ANALYSIS

(75) Inventors: Feng Zhao, Campbell; Andrew A. Berlin, San Jose; Elmer S. Hung, Foster City, all of CA (US)

(73) Assignee: Xerox Corporation, Stamford, CT (US)

( * ) Notice: Subject to any disclaimer, the term of this patent is extended or adjusted under 35 U.S.C. 154(b) by 0 days.

(21) Appl. No.: 09/510,366

(22) Filed: Feb. 22, 2000

(51) Int. Cl.[7] .................... G01H 11/08; G01M 1/22; G01M 13/04
(52) U.S. Cl. ............................... 7/659; 73/660
(58) Field of Search ................... 73/659, 660, 661, 73/593; 702/56

(56) References Cited

U.S. PATENT DOCUMENTS

| | | | | |
|---|---|---|---|---|
| 5,251,151 A | * | 10/1993 | Demjanenko et al. | 702/56 |
| 5,856,722 A | * | 1/1999 | Haronian et al. | 310/321 |
| 5,998,995 A | * | 12/1999 | Osiander et al. | 324/259 |
| 6,023,961 A | * | 2/2000 | Discenzo et al. | 73/54.01 |
| 6,128,961 A | * | 10/2000 | Haronian | 73/774 |
| 6,196,057 B1 | * | 3/2001 | Discenzo | 73/54.01 |
| 6,244,096 B1 | * | 6/2001 | Lewis et al. | 73/23.2 |

* cited by examiner

Primary Examiner—Hezron Williams
Assistant Examiner—Rose M. Miller
(74) Attorney, Agent, or Firm—Finnegan, Henderson, Farabow, Garrett & Dunner, LLP

(57) ABSTRACT

A MEMS-based system that enables low cost, low power, single chip realization of real-time signal detection and fault diagnosis. The system is suitable for analyzing the time-varying properties of a signal that are important for condition-based monitoring of electro-mechanical machines or structures. The system includes mechanical sensors that sense input signals such as vibration, signal templates of fault conditions, logic units that detect, store, and compare signal features to provide a diagnostic state, and an output readout mechanism to couple the diagnostic state to readout device that provides an external signal.

12 Claims, 6 Drawing Sheets

Level 5: 0, 0, 0, 0, 0, 0, 2, 2, 2, 0, 4, 4, 5, 5, 4, 2, 0, 1, 1, 1, 1, 1, 0, 0, 0, 1, 0, ...
Level 6: 0   3,   5,  10, 7,   5,   5,   5,   2,   3,   0,   4,   0, ...

MICROELECTROMECHANICAL MECHANISMS FOR REAL-TIME MECHANICAL VIBRATION SIGNATURE MONITORING AND ANALYSIS

FIELD OF THE INVENTION

The present invention relates generally to the field of signature analysis, and more particularly to a micromechanical sensor for real-time, time-frequency analysis of signals.

BACKGROUND OF THE INVENTION

Future electro-mechanical machines and structures will increasingly participate in their own service and maintenance using embedded distributed self-diagnostics that are remotely accessible to monitor machine health, detect and isolate subtle performance degradation, and in some cases even reconfigure some machines to adapt to changing operating environments. Traditionally, corrective maintenance and preventative maintenance have been the only two service paradigms. An estimate for the cost of service and maintenance for one major equipment manufacturer, however, is on the order of tens of billions of dollars. More recently, predictive or condition-based maintenance, enabled by low-cost sensors is emerging as an alternative.

Condition-based maintenance is just-in-time maintenance based on the actual health of the machine and its components. Since it avoids the cumulative cost of unnecessary service calls associated with preventative maintenance and the occurrence of machine failure and degradation associated with corrective maintenance, condition-based maintenance provides substantial cost savings.

Real-time signal analysis is critical for a variety of applications including condition-based monitoring and damage assessment for structures and electro-mechanical systems. Fault manifestation in machine vibration signals, however, is typically non-stationary in that the frequencies describing the faults vary over time. Identifying signatures of these types of faults requires analysis of properties of signals, such as frequency content, that vary over time. To isolate and identify a fault in a motor bearing, for example, the onset and temporal pattern of the changes in the spectral content of the signal must be determined. Traditional Fourier methods, including the short time Fourier transform (STFT), allows analysis of the time-varying properties of a signal that are important for diagnosis purposes.

Micro-Electro-Mechanical Systems (MEMS) integrate mechanical elements, such as microsensors and microactuators, and electronics on a common substrate through the utilization of microfabrication technology. MEMS are typically micromachined using integrated circuit (IC) compatible batch-processing techniques that selectively etch away parts of a silicon wafer or add new structural layers. They range in size from several micrometers to many millimeters. These systems sense, control, and actuate on a micro scale and function individually or in arrays to generate effects on a macro scale. MEMS sensors are known in the prior art and have been integrated into conventional non-MEMS signature analysis systems. The first problem with conventional systems is that sensors such as a tuning fork are not suitable for measuring time-varying spectral content of a signal because of the frequency-dependent damping constant of each individual fork. Second, the use of electronic processing in conventional systems make them susceptible to electronic interference. Third, the electronic processing requires adequate electrical power supply. Fourth, conventional systems are typically bulky in size because of the multitude of discrete component modules such as sensors, electronics, and readout. Thus, conventional systems are less portable than a monolithic MEMS implementation of the entire system.

In light of the foregoing, there is a need for a micromechanical sensor for signal detection an fault diagnosis that provides time-based windowing of event capture with control sequencing and data interpretation.

SUMMARY OF THE INVENTION

Accordingly, the present invention is directed to a MEMS system that allows real-time signal detection and fault diagnosis that substantially obviates one or more of the problems due to limitations and disadvantages of the related art.

In accordance with the purposes of the present invention, as embodied and broadly described, the invention provides a micro-electro-mechanical system for signature analysis including an array of sensors that measure a time varying event, wherein the array outputs a time-windowed sensor signal in response to operation of a system of interest. The sensor further includes a plurality of signal templates representing normal and faulty operating conditions of the system of interest, at least one logic unit that compares the sensor signal with the signal templates and provides a diagnostic state based on the comparison, and a readout device that outputs the diagnostic state as an external signal.

In another embodiment, the present invention provides a micro-electro-mechanical system for signature analysis of a system including an array of sensors detecting a physical phenomenon of interest, wherein the array of sensors has a time-frequency configuration that represents a template of a faulty operating condition of the system and a readout device that outputs an external signal indicating the faulty operating condition if the detected physical phenomenon matches the fault template.

The accompanying drawings are included to provide a further understanding of the invention and are incorporated in and constitute a part of this specification, illustrate several embodiments of the invention and together with the description serve to explain the principles of the invention.

BRIEF DESCRIPTION OF THE DRAWINGS

The accompanying drawings, which are incorporated in and constitute a part of this specification, illustrate an embodiment of the invention and, together with the description, serve to explain the objects, advantages, and principles of the invention.

DETAILED DESCRIPTION OF THE PREFERRED EMBODIMENTS

Reference will now be made in detail to the preferred embodiments of the invention, examples of which are illustrated in the accompanying drawings.

Figure 1:
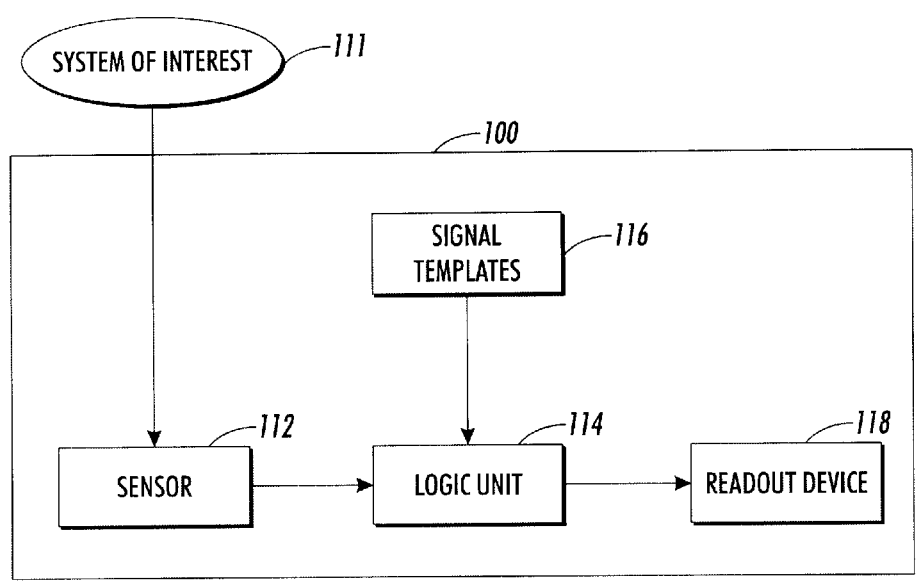
FIG. 1 is a block diagram representing the components of a signature analysis system consistent with the present invention.

FIG. 1 is a block diagram of the components of a signature analysis system consistent with the present invention. System 100 is preferably on a single semiconductor chip and includes sensor 112, logic unit 114, signal templates 116, and readout device 118.

Figure 2:
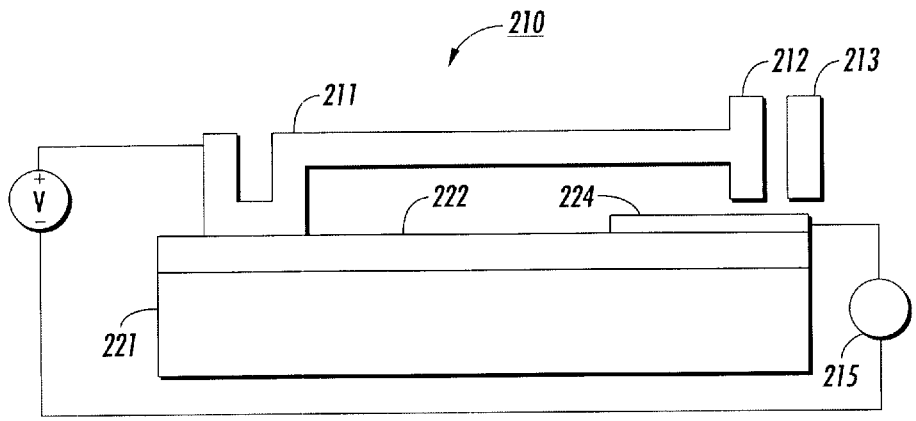
FIG. 2 is a schematic representation of a MEMS fabricated sensor for use in a signature analysis system consistent with the present invention.

In one embodiment sensor 112 is an array comprising a plurality of MEMS sensors responsive to a system of interest 111. Alternatively, sensor 112 can be a single sensor for a particular frequency. The system of interest can be a structure or an electro-mechanical machine. As shown in FIG. 2, sensor 210 is a MEMS fabricated device such as a tuning fork responsive to vibration from the electro-mechanical machine or structure. Sensor 210 has a fixed end 211 and a free end 212. Sensor 210 further includes substrate 221, insulating layer 222 on substrate 221, and bottom conductor 224 on a portion of insulating layer 222. Substrate 221 can be silicon or any other semiconductor base material. Sensor 210 responds to vibration near its resonant frequency by resonating at a higher amplitude at its free end. Although sensor 210 is described as a tuning fork to illustrate an embodiment of the present invention, sensor 210 can be any sensor responsive to, for example, shock, vibration, acceleration, temperature, pressure or electrical signals.

Sensor 210 further preferably includes a detector that detects and converts the resonance of the tuning forks into a sensor signal. Examples of such detectors include capacitive, piezoelectric, strain gauge, or other conventional detectors. FIG. 2 shows sensor 210 with capacitive detector 215. As free end 212 of sensor 210 moves, capacitive detector 215 senses the capacitive change between free end 212 of sensor 210 and bottom conductor 224.

In order to measure time-varying events of interest, sensors 210 preferably includes clamping or damping mechanisms, such as electrostatic clamp 213, to stop the movement of the free end of the resonant member. The clamping or damping mechanism effectively resets each sensor of array 112 and allows the temporal configuration of each sensor to be controlled. This provides the ability to do time-based windowing of event capture. Electrostatic clamp 213 allows sensors 210 to detect and then release (by clamping or damping) a frequency in order to track and readout time-varying frequency information in the system of interest. Other examples of such mechanisms include actively controlled open or closed loop vibration damping after releasing the tuning forks and tuning Q-factors by varying areas of electrodes.

Figure 3:
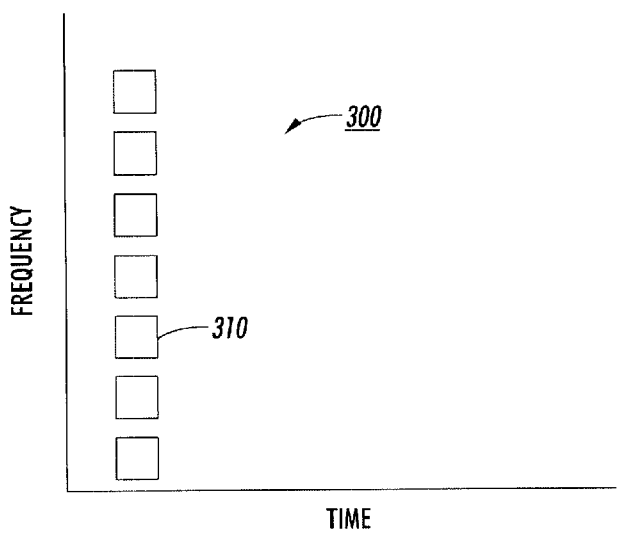
FIG. 3 is a schematic representation of a single array of sensors that are timed to measure frequency contents of a signal for each time window for use in a signature analysis system consistent with the present invention.

In another embodiment, a sensor array employs a plurality of sensors each having a different resonant frequency preferably with a clamping or damping mechanism. As shown in FIG. 3, a frequency spectrum of the detected physical phenomenon of interest can be constructed using array 300 comprising a plurality of sensors 310 having different resonant frequencies. In this embodiment, the signal from each sensor 310 represents a portion of the frequency spectrum.

Figure 4:
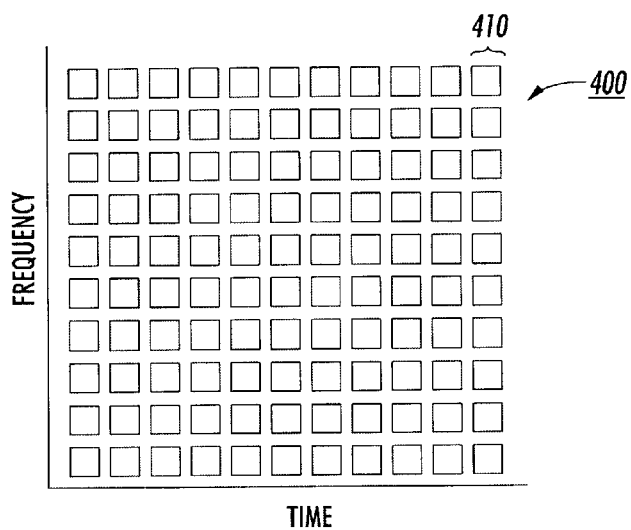
FIG. 4 is a schematic representation of a plurality of sensor arrays which are timed to measure frequency content for different time windows for use in a signature analysis system consistent with the present invention.

In another embodiment shown in FIG. 4, sensor 400 comprises a plurality of sensor arrays 410. This embodiment is preferred when the time-varying content of the signal is significantly faster than the tuning fork damping constant of the MEMS device. In this embodiment, each array of sensors detects the frequency content of a signal for a particular time window. Different arrays are timed to activate at fixed time intervals apart from each other. Once an array is read out, the oscillation of the tuning forks in the array is clamped or damped so that it can be activated to record new frequency content at a subsequent time interval. The number of arrays depends on the damping constant as well as the rate at which the time-varying components of the signal change.

Figure 5:
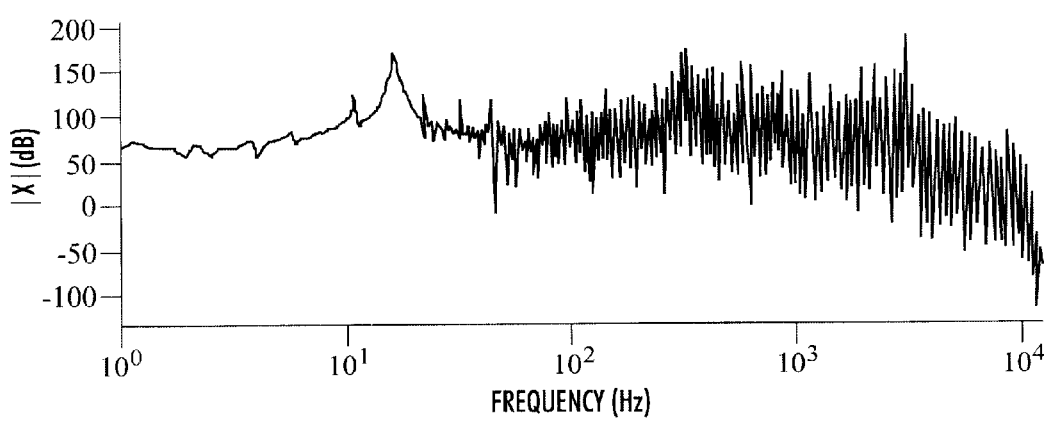
FIG. 5 is a spectral analysis of a paper drive plate vibration in a Xerox copying system having a motor unbalance fault.

An example of a vibration signal having time-varying frequency information is shown in FIG. 5. The vibration signal shown in FIG. 5 is from a paper drive plate of a Xerox copying system having a fault due to unbalance in the main drive motor. The main frequency content of the signal is primarily in the 10 Hz to 1 kHz range. The time-varying components of the frequency content due to the unbalance of the main motor is around 10 Hz to 1 kHz.

Referring back to FIG. 1, logic unit 114 compares the sensor signal to stored signal templates 116. Stored signal templates 116 represent, for example, normal operating conditions and potential fault conditions of the electro-mechanical machine or structure. If multiple sensor arrays are used as shown in FIG. 4, logic unit 114 comprises a plurality of logic units wherein one unit is coupled to each sensor array. The output from the plurality of logic units 114 is compared against an event sequence template and the results are aggregated.

Figure 6:
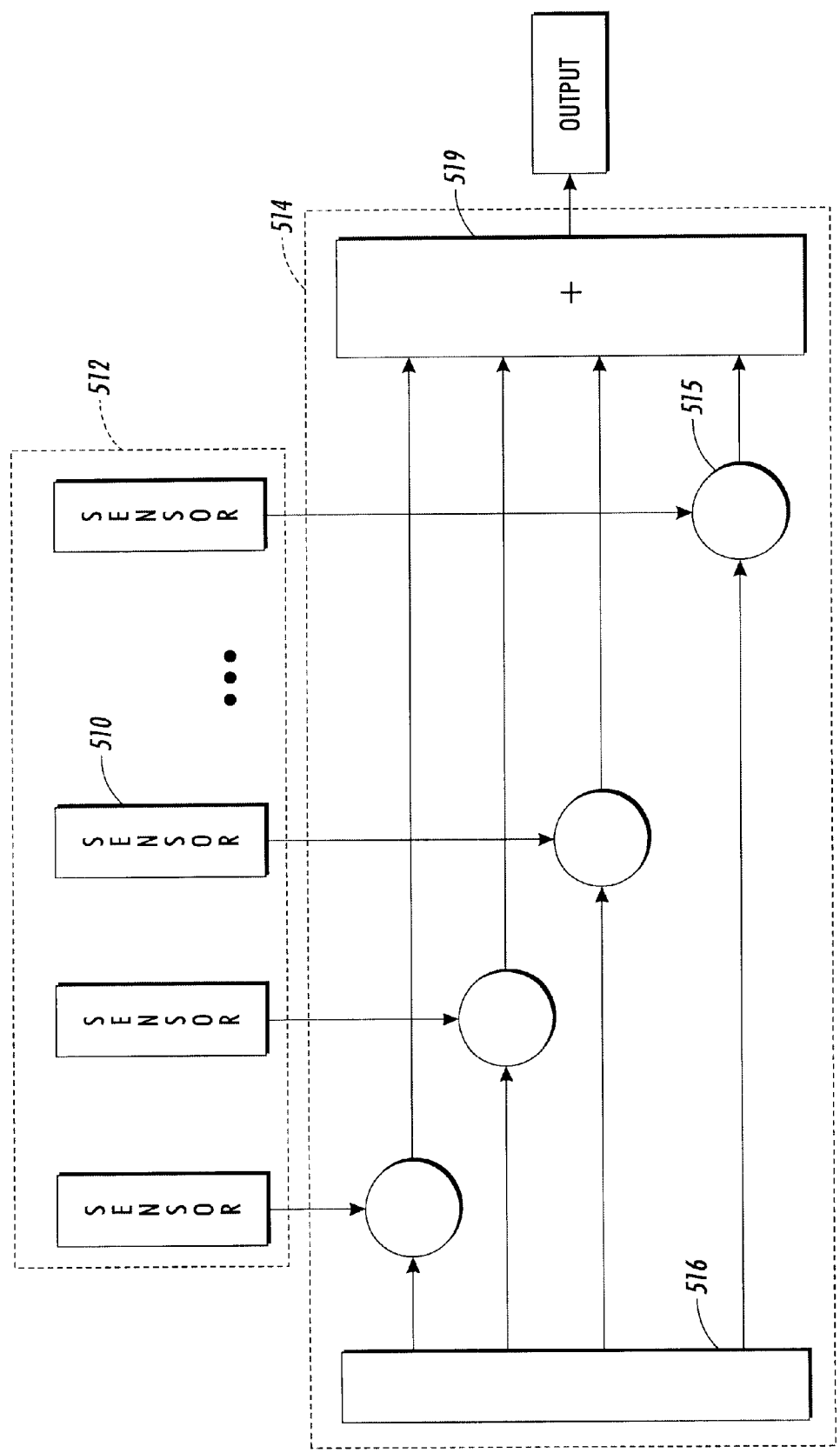
FIG. 6 is a schematic of an electronic logic unit consistent with the present invention.

Logic unit 114 is preferably an electronic component that stores signal templates 116 of fault conditions and performs the comparison. As shown in FIG. 6, an example of logic unit 614 comprises multiple bit comparators 615, each of which can be coupled to each sensor 610 in array 612. The readout from each sensor 610 is compared with a corresponding bit of stored bit pattern 616 using bit comparator 615. An adder 619 connecting the output of comparators sums the differences and reports detection results by examining the total difference. In detection applications where only templates for normal conditions are known, a fault condition is reported if the total difference exceeds a predetermined threshold. In signal discriminate analysis where normal and faulty conditions are known, a detection is reported when the total difference is within a preset tolerance. This can be accomplished, for example, by cycling the comparison through all the templates until a match is reported.

When detecting time varying spectral content of signals using the single sensor array, an additional counter, preferably an electronic component, is necessary to record the sequence of detection events. When using multiple sensor arrays, the output of multiple logic units activated at consecutive time intervals is compared with a stored event sequence template to determine if a particular fault signal sequence is present or not.

Figure 7:
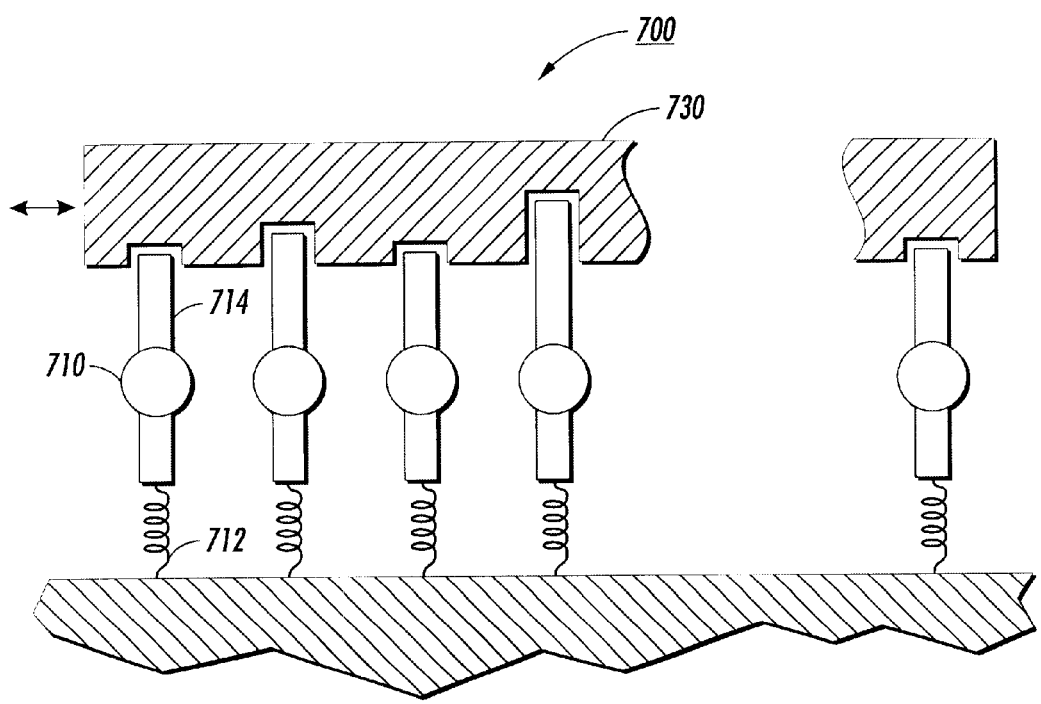
FIG. 7 is a schematic representation of a mechanical logic unit.

In another embodiment, logic unit 114 stores the sensor signal as a mechanical state or position and counts signal events using MEMS fabricated gates, relays, and gears. Logic unit 116 compares the mechanically stored signal with signal templates of fault conditions 116 using mechanical logic implementations. An example of a mechanical logic implementation is shown in FIG. 7. Sensor 700 comprises a plurality of sensors 710 each comprising restoring springs 712 attached to pins 714. Pins 714 restrain gate mechanism 730 from traveling to a set mechanical state. The displacement required to pull pins 714 from gate 730 is pre-calibrated. Once pins 714 are pulled out, gate 730 is free to travel in the direction shown by the arrow to its set mechanical state indicting that a particular combinations of sensor readings is present.

Figure 8:
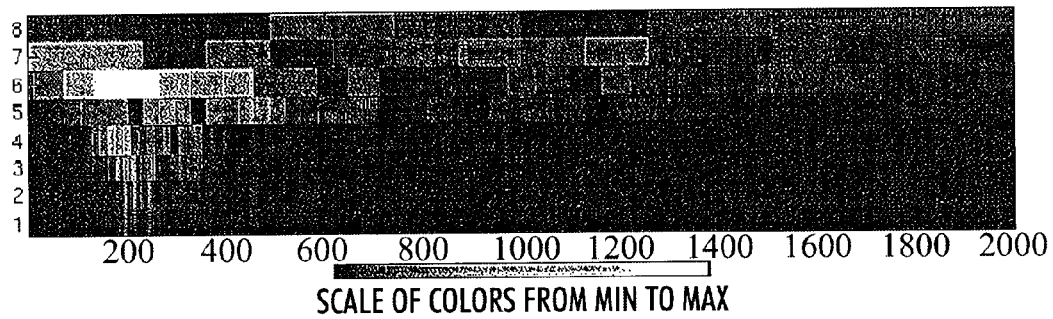
FIG. 8 is a signal template extracted from the vibration signal of a paper drive assembly in a Xerox copying system.

Signal templates of fault conditions 116 are preferably time-frequency signal templates recorded as bit sequences. They are typically extracted from diagnostic data generated from lifetime tests of the system of interest. Since the diagnostic data includes normal and faulty operating conditions, the templates of faulty operation are useful for detecting and isolating fault occurrence. Signal templates 116 can be extracted from diagnostic data using techniques such as wavelet analysis and short time Fourier transform (STFT). FIG. 8 shows an example of a signal template extracted from the vibration signal of a paper drive assembly in a Xerox copying system having a defective solenoid using wavelet analysis.

Based on the comparison, logic unit 114 provides a diagnostic state to readout device 118. Readout device couples the diagnostic state to an external signal that can be read by another system or a human being. A human readable signal is, for example, a modulated LED. A signal readable by another system is, for example, an optical signal from a vertical cavity surface emitting laser (VCSEL).

Figure 9:
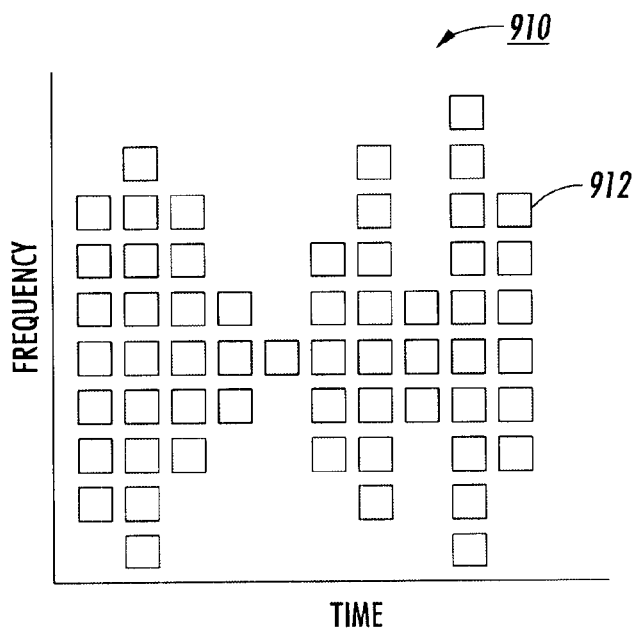
FIG. 9 is a schematic representation of an array of sensors where the spatial and frequency configuration of the sensors match that of a known operating fault.

Another embodiment consistent with the present invention is shown in FIG. 9. This signature analysis system comprises an array of sensors 910 where the sensors themselves, timed to activate at different times, represent a template of a faulty operating condition. In other words, the temporal and frequency configuration of sensors 912 in the array match the time-frequency components of a signal of a known faulty operating condition. In this embodiment, the frequency and spatial configuration of sensors 912 in array 910 match a known fault, such as a vibration signal due to a faulty solenoid in the main drive plate of a copying system. During normal operation of the copying system, the time-frequency components of the vibration signal do not correspond to the temporal and frequency configuration of sensors 912.

During faulty operation, however, the time-frequency components of the vibration match the temporal and frequency configuration of sensors 912. As each sensor of array 910 is activated, a mechanical logic unit (not shown) records the sensor's activation by, for example, movement of a gear, positioning of a relay, sliding of a linear slider element, mechanical movement of particles distributed on a surface, opening a fluidic valve to permit fluid pressure to store a record of the sensors activation, closing of an electrical contact, mechanical movement exposing or masking an optical source or reflector. Once all of the sensors 912 in array 910 representing the known fault condition are activated, the mechanical logic unit determines that the system is operating in the known fault condition. A readout device (not shown) then outputs a signal indicating the faulty operating condition. The signature analysis system preferably includes multiple sensor arrays that represent multiple known fault conditions.

In another embodiment, a portable signature analysis system is provided including an array of sensors, a plurality of stored signal templates, at least one logic unit, and a readout component. The sensor array outputs a sensor signal in response to operation of a system of interest. The portable system stores a plurality of signal templates representing normal and faulty operating conditions of the system of interest. Once a signal is detected, one or more logic units compare the detected sensor signal with the stored signal templates and provides a diagnostic state based on the comparison. Once the diagnostic state is determined, a readout component displays the diagnostic state in a human readable form.

It will be apparent to those skilled in the art that various modifications and variations can be made in the system level sensor that relies on mechanical component implementation and integration for real-time signal detection and fault diagnosis. Thus, it is intended that the present invention cover the modifications and variations of this invention provided they come within the scope of the appended claims and their equivalents.

What is claimed is:

1. A micro-electro-mechanical system for signature analysis comprising:

an array of sensors that measure a time varying event, wherein the array outputs a time-windowed sensor signal in response to operation of a system of interest;

a plurality of signal templates representing normal and faulty operating conditions of the system of interest;

at least one logic unit that compares the sensor signal with the signal templates, and provides a diagnostic state based on the comparison; and a readout device that outputs the diagnostic state as an external signal.

2. The micro-electro-mechanical system of claim 1, wherein the sensor signal is mechanically stored.

3. The micro-electro-mechanical system of claim 1, wherein the comparison is performed by at least one bit comparator that compares the sensor signal to a stored bit pattern representing the signal template.

4. The micro-electro-mechanical system of claim 1, wherein the readout device outputs the diagnostic signal in human-readable form.

5. The micro-electro-mechanical system of claim 1, wherein each sensor of the array has a programable temporal configuration.

6. The micro-electro-mechanical system of claim 5, where each sensor of the array includes clamps to modify the temporal configuration of the sensor.

7. The micro-electro-mechanical system of claim 5, wherein the clamps reset the sensors and the sensors output a subsequent time-windowed sensor signal in response to operation of the system of interest.

8. The micro-electro-mechanical system of claim 1, wherein the sensor array comprises a plurality of sensors each having a different resonant frequency and temporal configuration to detect and read-out time varying frequency information from the system of interest.

9. The micro-electro-mechanical system of claim 2, wherein the signal templates are stored in mechanical memories and compared to the sensor signal using a mechanical logic implementation.

10. The micro-electro-mechanical system of claim 1, further including a plurality of arrays, wherein each array measures the frequency content of a different time window of the operation of the system of interest.

11. The micro-electro-mechanical system of claim 1, wherein the micro-electro-mechanical system is on a single semiconductor chip.

12. A portable signature analysis system comprising:

an array of MEMS sensors that detect a time varying event, wherein the array outputs a time-windowed sensor signal in response to operation of a system of interest;

a plurality of stored signal templates representing normal and faulty operating conditions of the system of interest;

at least one logic unit that compares the sensor signal with the stored signal templates, and provides a diagnostic state based on the comparison; and a readout component that outputs the diagnostic state in a human readable form.

* * * * *